(12) United States Patent
Syverson et al.

(10) Patent No.: US 7,118,759 B2
(45) Date of Patent: Oct. 10, 2006

(54) ABSORBENT ARTICLES CONTAINING ADDITIVES

(75) Inventors: Rae Ellen Syverson, Fond du Lac, WI (US); Richard A. Proctor, Madison, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 525 days.

(21) Appl. No.: 10/271,513

(22) Filed: Oct. 16, 2002

(65) Prior Publication Data

US 2003/0157149 A1    Aug. 21, 2003

Related U.S. Application Data

(60) Provisional application No. 60/331,971, filed on Nov. 21, 2001, provisional application No. 60/331,937, filed on Nov. 21, 2001.

(51) Int. Cl.
*A01N 25/34* (2006.01)
*A61F 6/06* (2006.01)
*A61F 13/02* (2006.01)

(52) U.S. Cl. ............... 424/404; 424/411; 424/430; 424/431

(58) Field of Classification Search ............ 424/404, 424/411, 430, 431
See application file for complete search history.

(56) References Cited

U.S. PATENT DOCUMENTS

| | | | |
|---|---|---|---|
| 5,547,985 | A | 8/1996 | Brown-Skrobot et al. |
| 5,686,088 | A | 11/1997 | Mitra et al. |
| 6,346,391 | B1 | 2/2002 | Oethinger et al. |
| 2003/0100871 | A1 | 5/2003 | Mauro et al. |
| 2005/0113448 | A1* | 5/2005 | Syverson et al. ......... 514/546 |

OTHER PUBLICATIONS

D'Agnolo, et al., Inhibition of fatty acid synthesis by the antibiotic cerulenin: Specific inactivation of β-ketoacyl-acyl carrier protein synthetase, Biochimica et Biophysica Acta, 1973, pp. 155-166, vol. 326.

Altenbern, R.A., Extreme sensitivity of staphylococcal enterotoxin B and C production to inhibition by cerulenin, Antimicrobial Agents and Chemotherapy, 1977, pp. 906-908, vol. 11.

Pepper, et al., Studies on the effect of inhibition of lipid biosynthesis by cerulenin on the production of staphylococcal enterotoxin A, Staphylococci and staphylococcal infections, 1981, pp. 393-396, Zbl. Bakt. Suppl. 10, Gustav-Fisher Verlag, Stuttgart, New York.

Campbell, et al., Bacterial fatty acid biosynthesis: targets for antibacterial drug discovery, Annual Review of Microbiology, 2001, pp. 305-313, vol. 55, issue 1.

Price, et al., Inhibition of β-ketoacyl-acyl carrier protein synthases by thiolactomycin and cerulenin, J. Biological Chemistry, 2001, pp. 6551-6559, vol. 276, No. 9.

Mehesz, Erno, Pharmaceutical Compositions for the Prevention and Treatment of Fluoralbus, 81CA:54468, 1974 (1 page).

Fast, David J., et al., Toxic Shock Syndrome-Associated Staphylococcal and Streptococcal Pyrogenic Toxins are Potent Inducers of Tumor Necrosis Factor Production, 110CA:73618, 1989 (1 page).

Gennaro, et al., Remington's Pharmaceutical Sciences, 17th ed., 1985, pp. 1498-1499.

Regoes, J., et al., Antimicrobial Specturm of Triclosan, a Broad-Spectrum Antimicrobial Agent for Topical Application, 91CA:747, 1979 (1 page).

Adesiyun, et al., "Characteristics of Staphylococcus aureus strains isolated from clinical and non-clinical human sources in Trinidad: susceptibility to bacteriophages and antimicrobial agents, and toxigenicity," Zentralblatt fuer Bakteriologie, vol. 282, No. 4 (1995) (abstract), 124:112182.

Bory, et al., "Germicide," 82CA:18932 (1975) (abstract).

Siddiqui, et al., "Pharmacokinetics of triclosan in rat after intravenous and intravaginal administration," Journal of Environmental Pathology and Toxicology, vol. 2, No. 3 (1979) (abstract), 90:197346.

Suller, et al., "Triclosan and antibiotic resistance in *Staphylococcus aureus*," Journal of Antimicrobial Chemotherapy, 2000, pp. 11-18, vol. 46.

Heath, et al., Inhibition of the *Staphylococcus aureus* NADPH-dependent Enoyl-Acyl Carrier Protein Reductase by Triclosan and Hexachlorophene, Journal of Biological Chemistry, 2000, pp. 4654-4659, vol. 275, No. 7.

* cited by examiner

*Primary Examiner*—Carlos A. Azpuru
(74) *Attorney, Agent, or Firm*—Senniger Powers

(57) ABSTRACT

Effective amounts of the inhibitory compounds described herein capable of significantly reducing the production of TSST-1 are as follows: (1) compounds of Structure (I): from about 0.0001 micromoles/gram absorbent product to about 0.08 micromoles/gram absorbent product, desirably from about 0.0005 micromoles/gram of absorbent product to about 0.05 micromoles/gram of absorbent product; and (2) compounds of Structures (II) and (III): from about 0.05 micromoles/gram of absorbent product to 5 micromoles/gram of absorbent product, desirably from about 0.1 micromoles/gram of absorbent product to about 1 micromole/gram of absorbent product. Specifically, effective amounts of hexachlorophene include from about 0.00024 micromoles/gram of absorbent product to about 0.08 micromoles/gram of absorbent product, desirably from about 0.001 micromoles/gram of absorbent product to about 0.05 micromoles/gram of absorbent product. Specifically, effective amounts of triclosan include from about 0.0005 micromoles/gram of absorbent product to about 0.03 micromoles/gram of absorbent product. Specifically, effective amounts of cerulenin include from about 0.1 micromoles/gram of absorbent product to about 1 micromole/gram of absorbent product.

19 Claims, No Drawings

ABSORBENT ARTICLES CONTAINING ADDITIVES

REFERENCE TO RELATED APPLICATIONS

This patent application claims the benefit of U.S. Provisional Patent Application Ser. No. 60/331,971, filed on Nov. 21, 2001, and U.S. Provisional Patent Application Ser. No. 60/331,937, filed on Nov. 21, 2001. The entire contents of these provisional applications are incorporated herein by reference.

BACKGROUND OF THE INVENTION

The present invention relates to inhibiting the production of toxic shock syndrome toxin one (TSST-1) by *Staphylococcus aureus*. More particularly, the present invention relates to inhibiting the production of TSST-1 in the presence of absorbent articles such as vaginal and nasal tampons, sanitary napkins, wound dressings, and diapers, by incorporating certain compounds into the absorbent articles having an inhibitory effect on Gram-positive bacteria and the production of TSST-1.

Disposable absorbent articles for the absorption of human exudates, such as catamenial tampons, are widely used. These disposable articles typically have a compressed mass of absorbent material formed into the desired shape, which is typically dictated by the intended consumer use. In the case of a menstrual tampon, the device is intended to be inserted in the vaginal cavity for absorption of body fluids generally discharged during a woman's menstrual period.

There exists in the female body a complex process which maintains the vagina and physiologically related areas in a healthy state. In a female between the age of menarche and menopause, the normal vagina provides an ecosystem for a variety of microorganisms. Bacteria are the predominant type of microorganism present in the vagina; most women harbor about $10^9$ bacteria per gram of vaginal fluid. The bacterial flora of the vagina is comprised of both aerobic and anaerobic bacteria. The more commonly isolated bacteria are *Lactobacillus* species, *Corynebacteria*, *Gardnerella vaginalis*, *Staphylococcus* species, *Peptococcus* species, aerobic and anaerobic *Streptococcus* species, and *Bacteroides* species. Other microorganisms that have been isolated from the vagina on occasion include yeast (*Candida albicans*), protozoa (*Trichomonas vaginalis*), mycoplasma (*Mycoplasma hominis*), chlamydia (*Chlamydia trachomatis*), and viruses (Herpes simplex). These latter organisms are generally associated with vaginitis or venereal disease, although they may be present in low numbers without causing symptoms.

Physiological, social, and idiosyncratic factors effect the quantity and species of bacteria present in the vagina. Physiological factors include age, day of the menstrual cycle, and pregnancy. For example, vaginal flora present in the vagina throughout the menstrual cycle can include lactobacilli, *corynebacterium*, ureaplasma, and mycoplasma. Social and idiosyncratic factors include method of birth control, sexual practices, systemic disease (e.g., diabetes), and medications.

Bacterial proteins and metabolic products produced in the vagina can effect other microorganisms and the human host. For example, the vagina between menstrual periods is mildly acidic having a pH ranging from about 3.8 to about 4.5. This pH range is generally considered the most favorable condition for the maintenance of normal flora. At that pH, the vagina normally harbors numerous species of microorganisms in a balanced ecology, playing a beneficial role in providing protection and resistance to infection and makes the vagina inhospitable to some species of bacteria such as *Staphylococcus aureus* (*S. aureus*). The low pH is a consequence of the growth of lactobacilli and their production of acidic products. Microorganisms in the vagina can also produce antimicrobial compounds such as hydrogen peroxide and bactericides directed at other bacterial species. One example is the lactocins, bacteriocin-like products of lactobacilli directed against other species of lactobacilli.

Some microbial products produced in the vagina may negatively affect the human host. For example, *S. aureus* is a bacteria that commonly colonizes human skin and mucous membranes. It causes disease in humans through invasion or through the production of toxic proteins. One such disease is toxic shock syndrome (TSS), caused by toxic shock syndrome toxin-1 (TSST-1) and other similar toxins. When absorbed into the blood stream, TSST-1 produces TSS in non-immune humans. An increased incidence of TSS is associated with growth of *S. aureus* in the presence of tampons, such as those used in nasal packing or as catamenial devices.

*S. aureus* is found in the vagina of approximately 16% of healthy women of menstrual age. Approximately 25% of the *S. aureus* isolated from the vagina are found to produce TSST-1. TSST-1 has been identified as causing TSS in humans.

Symptoms of TSS generally include fever, diarrhea, vomiting and a rash followed by a rapid drop in blood pressure. Multiple organ failure occurs in approximately 6% of those who contract the disease. *S. aureus* does not initiate TSS as a result of the invasion of the microorganism into the vaginal cavity. Instead as *S. aureus* grows and multiplies, it can produce TSST-1. Only after entering the bloodstream does TSST-1 toxin act systemically and produce the symptoms attributed to TSS.

Menstrual fluid has a pH of about 7.3. During menses, the pH of the vagina moves toward neutral and can become slightly alkaline. This change permits microorganisms whose growth is inhibited by an acidic environment the opportunity to proliferate. For example, *S. aureus* is more frequently isolated from vaginal swabs during menstruation than from swabs collected between menstrual periods.

When *S. aureus* is present in an area of the human body that harbors a normal microbial population such as the vagina, it may be difficult to eradicate the *S. aureus* bacteria without harming members of the normal microbial flora required for a healthy vagina. Typically, antibiotics that kill *S. aureus* are not an option for use in catamenial products because of their effect on the normal vaginal microbial flora and their propensity to stimulate toxin production if all of the *S. aureus* are not killed. An alternative to eradication is technology designed to prevent or substantially reduce the bacteria's ability to produce toxins.

There have been numerous attempts to reduce or eliminate pathogenic microorganisms and menstrually occurring TSS by incorporating into a tampon pledget one or more biostatic, biocidal, and/or detoxifying compounds. For example, L-ascorbic acid has been applied to a menstrual tampon to detoxify toxin found in the vagina. Others have incorporated monoesters and diesters of polyhydric aliphatic alcohols, such as glycerol monolaurate, as biocidal compounds (see, e.g., U.S. Pat. No. 5,679,369). Still others have introduced other non-ionic surfactants, such as alkyl ethers, alkyl amines, and alkyl amides as detoxifying compounds (see, e.g., U.S. Pat. Nos. 5,685,872, 5,618,554, and 5,612,045).

Despite the aforementioned attempts, there continues to be a need for compounds that will effectively inhibit the production of TSST-1 from Gram positive bacteria, and maintain activity even in the presence of the enzymes lipase and esterase which can have adverse effects on potency and which may also be present in the vagina. Further, it is desirable that the detoxifying compounds useful in the inhibition of the production of TSST-1 be substantially non-harmful to the natural flora found in the vaginal area.

SUMMARY OF THE INVENTION

It is a general object of the present invention to provide an absorbent article which inhibits the production of TSST-1 from Gram positive bacteria. A more specific object of the present invention is to provide a catamenial tampon incorporating one or more compounds which inhibit fatty acid biosynthesis and inhibit the production of TSST-1.

Another object of the present invention is to provide a catamenial tampon incorporating one or more inhibitory compounds as described herein in combination with one or more other inhibitory ingredients such as, but not limited to, for example, aromatic compounds, isoprenoid compounds, laureth-4, PPG-5 lauryl ether, 1-0-dodecyl-rac-glycerol, disodium laureth sulfosuccinate, glycerol monolaurate, alkylpolyglycosides, polyethylene oxide (2) sorbital ether or myreth-3-myristate which in combination act to substantially inhibit the production of TSST-1 by *S. aureus*.

A further object of the present invention is to provide a catamenial tampon that has incorporated therein one or more compounds that will inhibit the production of TSST-1 from Gram positive bacteria without significantly imbalancing the natural flora present in the vaginal tract.

The present invention is based on the discovery that compounds that inhibit fatty acid biosynthesis in bacteria also inhibit TSST-1 production in bacteria. Specifically, when one or more inhibitory compounds (used alone or in combination with other inhibitory compounds) having the structure of any one of (I)–(III) are incorporated into an absorbent article, such as a catamenial tampon, the production of TSST-1 in Gram positive bacteria is substantially inhibited.

(I)

[Structure I: biphenyl compound with substituents $R_{100}$, $R_{102}$, $R_{103}$, $R_{104}$, $R_{105}$, $R_{106}$, $R_{107}$, $R_{108}$ and linker V']

OR (II)

[Structure II: $R_{200}$—C(O)—epoxide—C(O)—$NH_2$]

OR (III)

[Structure III: cerulenin closed form with $R_{200}$, HO, epoxide, and lactam N–H]

wherein V' is selected from —NH—, —O—, —CH$_2$—, —C(O)OCH$_2$—, —C(O)—, and —C(O)O—, $R_{100}$, $R_{102}$, $R_{103}$, $R_{104}$, $R_{105}$, $R_{106}$, $R_{107}$ and $R_{108}$ are independently selected from hydrogen, halogen, —OH, —O($R_{113}$), —SO$_3$Na, —SO$_3$H, —N($R_{114}$)($R_{115}$), and —NO$_2$, $R_{113}$ is selected from hydrogen, sodium and a monovalent saturated or unsaturated, substituted or unsubstituted hydrocarbyl moiety having from 1 to 10 carbon atoms which may or may not be interrupted with a heteroatom, $R_{114}$ and $R_{115}$ are independently selected from hydrogen and a saturated or unsaturated, substituted or unsubstituted hydrocarbyl moiety having from 1 to 10 carbon atoms which may or may not be interrupted with a heteroatom, and $R_{200}$ is a monovalent, saturated or unsaturated, substituted or unsubstituted hydrocarbyl moiety having from 1 to 15 carbon atoms which may or may not be interrupted with a heteroatom.

Preferred compounds of Structure (I) above for use in accordance with the present invention include hexachlorophene (CAS No. 70-30-4), benzylparaben (CAS No. 94-18-8), benzyl salicylate (CAS No. 118-58-1), benzophenone-6 (CAS No. 131-54-4), benzophenone-7 (CAS No. 85-19-8), benzophenone-8 (CAS No. 131-53-3), benzophenone-9 (CAS No. 3121-60-6), benzophenone-10 (CAS No. 1641-17-4), benzophenone-12 (CAS No. 1843-05-6), benzophenone-1 (CAS No. 131-56-6), benzophenone-2 (CAS No. 131-55-5), benzophenone-3 (CAS No. 131-57-7), chlorophene (CAS No. 120-32-1), 2,4-diaminodiphenylamine (CAS No. 136-17-4), dichlorophene (CAS No. 97-23-4), HC Green No. 1 (CAS No. 52136-25-1), HC Orange No. 1 (CAS No. 54381-08-7), HC Red No. 1 (CAS No. 2784-89-6), triclosan (CAS No. 3380-34-5), isopropylbenzylsalicylate (below)

[Structure: salicylate ester — 2-hydroxyphenyl–C(O)–OCH$_2$–phenyl–CH(CH$_3$)$_2$]

and phenyl salicylate (CAS No. 118-55-8). Particularly preferred compounds of Structure (I) include triclosan and hexachlorophene.

Preferred compounds of Structures (II) and (III) include cerulenin (open structure) and cerulenin (closed structure), respectively.

Other objects and advantages of the present invention, and modifications thereof, will become apparent to persons skilled in the art without departure from the inventive concepts defined in the claims.

DETAILED DESCRIPTION OF THE PREFERRED EMBODIMENTS

In accordance with the present invention, it has been discovered that certain compounds as described herein can be incorporated into or onto an absorbent article, such as a catamenial tampon, to substantially inhibit the production of TSST-1 from Gram positive bacteria. The compounds as described herein can be used in combination with surface-active agents such as, for example, compounds with an ether, ester, amide, glycosidic, or amine bond linking a $C_8$–$C_{18}$ fatty acid to an aliphatic alcohol, polyalkoxylated sulfate salt, or polyalkoxylated sulfosuccinic salt, to substantially inhibit the production of TSST-1 from Gram positive bacteria. Through vigorous research and experimentation, it has been discovered that, surprisingly, compounds that inhibit certain fatty acid synthesis routes in bacteria also inhibit the production of TSST-1 by *S. aureus*. Specifically, compounds that inhibit fatty acid II enzymes in other bacterial species appear to inhibit their *S. aureus* homologues.

This invention will be described herein in detail in connection with a catamenial tampon, but will be understood by persons skilled in the art to be applicable to other disposable absorbent articles such as sanitary napkins, panty liners, adult incontinence garments, diapers, medical bandages and tampons such as those intended for medical, dental, surgical, and/or nasal use wherein the inhibition of TSST-1 from Gram positive bacteria would be beneficial. As used herein, the term "absorbent article" generally refers to devices comprising an absorbent material, such as a fibrous absorbent material, which absorbs and contains body fluids, and more specifically, refers to devices which are placed against or near the skin and/or mucosa to absorb and contain the various fluids discharged from the body. The term "disposable" is used herein to describe absorbent articles that are not intended to be laundered or otherwise restored or reused as an absorbent article after a single use. Examples of such disposable absorbent articles include, but are not limited to, health care related products including bandages and tampons such as those intended for medical, dental, surgical and/or nasal use; personal care absorbent products such as feminine hygiene products (e.g., sanitary napkins, panty liners, and catamenial tampons), diapers, training pants, incontinent products and the like, wherein the inhibition of the production of TSST-1 from Gram positive bacteria would be beneficial.

Catamenial tampons suitable for use with the present invention are typically made of absorbent fibers, including natural and synthetic fibers. Catamenial tampons are typically made in the form of an elongated cylindrical form in order that they may have a sufficiently large body of material to provide the required absorbing capacity, but may be made in a variety of sizes and shapes such that the tampon may be easily inserted into the vaginal cavity. The tampon may or may not be compressed, although compressed types are now generally preferred. The tampon may be made of various fiber blends including both absorbent and nonabsorbent fibers. Suitable absorbent fibers include, for example, cellulosic fibers such as cotton and rayon. Fibers may be 100% cotton, 100% rayon, a blend of cotton and rayon, or other absorbent materials known to be suitable for tampon use. The tampon may or may not have a cover or wrapper. Suitable methods and materials for the production of tampons and other absorbent articles are well known to those skilled in the art.

It has been discovered that certain compounds can substantially inhibit the production of TSST-1 by Gram positive bacteria and, specifically, the production of TSST-1 from *S. aureus* bacteria. The inhibitory compounds useful in the practice of the present invention have the general chemical structure:

(I)

[Structure I: two phenyl rings connected by V' with substituents $R_{100}$, $R_{102}$, $R_{103}$, $R_{104}$, $R_{105}$, $R_{106}$, $R_{107}$, $R_{108}$]

OR

-continued (II)

[Structure II: $R_{200}$—C(O)—epoxide—C(O)—NH$_2$]

OR (III)

[Structure III: $R_{200}$, HO, epoxide-lactam ring]

wherein V' is selected from —NH—, —O—, —CH$_2$—, —C(O)OCH$_2$—, —C(O)—, and —C(O)O—, $R_{100}$, $R_{102}$, $R_{103}$, $R_{104}$, $R_{105}$, $R_{106}$, $R_{107}$ and $R_{108}$ are independently selected from hydrogen, halogen, —OH, —O($R_{113}$), —SO$_3$Na, —SO$_3$H, —N($R_{114}$)($R_{115}$), and —NO$_2$, $R_{113}$ is selected from hydrogen, sodium and a monovalent saturated or unsaturated, substituted or unsubstituted hydrocarbyl moiety having from 1 to 10 carbon atoms which may or may not be interrupted with a heteroatom, and $R_{114}$ and $R_{115}$ are independently selected from hydrogen, and a saturated or unsaturated, substituted or unsubstituted hydrocarbyl moiety having from 1 to 10 carbon atoms which may or may not be interrupted with a heteroatom, and $R_{200}$ is a monovalent, saturated or unsaturated, substituted or unsubstituted hydrocarbyl moiety having from 1 to 15 carbon atoms which may or may not be interrupted with a heteroatom.

Preferred compounds of Structure (I) above for use in accordance with the present invention include hexachlorophene (CAS No. 70-30-4), benzylparaben (CAS No. 94-18-8), benzyl salicylate (CAS No. 118-58-1), benzophenone-6 (CAS No. 131-54-4), benzophenone-7 (CAS No. 85-19-8), benzophenone-8 (CAS No. 131-53-3), benzophenone-9 (CAS No. 3121-60-6), benzophenone-10 (CAS No. 1641-17-4), benzophenone-12 (CAS No. 1843-05-6), benzophenone-1 (CAS No. 131-56-6), benzophenone-2 (CAS No. 131-55-5), benzophenone-3 (CAS No. 131-57-7), chlorophene (CAS No. 120-32-1), 2,4-diaminodiphenylamine (CAS No. 136-17-4), dichlorophene (CAS No. 97-23-4), HC Green No. 1 (CAS No. 52136-25-1), HC Orange No. 1 (CAS No. 54381-08-7), HC Red No. 1 (CAS No. 2784-89-6), triclosan (CAS No. 3380-34-5), isopropylbenzylsalicylate (below)

[Structure: phenyl ring with OH, —C(=O)—OCH$_2$—phenyl—CH(CH$_3$)$_2$]

or phenyl salicylate (CAS No. 118-55-8). Particularly preferred compounds of Structure (I) include triclosan and hexachlorophene.

Preferred compounds of Structures (II) and (III) include cerulenin (open structure) and cerulenin (closed structure), respectively.

The hydrocarbyl moieties described herein include both straight chain and branched chain hydrocarbyl moieties and may or may not be substituted with halogens, for example, and/or interrupted with hetero atoms such as nitrogen, sulfur, and oxygen, for example. One skilled in the art will recognize that one or more of the compounds or structures set forth herein can exist in one or more isomers which are also part of the present invention. Also, one or more of the compounds set forth herein may exist as salts, which are also part of the present invention.

The absorbent article includes the inhibitory compounds described herein in an amount effective to substantially inhibit the formation of TSST-1 when the absorbent article is exposed to *S. aureus* bacteria. Several methods are known in the art for testing the effectiveness of potential inhibitory agents on the inhibition of the production of TSST-1 by *S. aureus*. One such preferred method is set forth in Example 1 below. When tested in accordance with the testing methodology described herein, the inhibitory compounds preferably reduce the formation of TSST-1 when the absorbent article is exposed to *S. aureus* by at least about 40%, more preferably by at least about 50%, still more preferably by at least about 60%, still more preferably by at least about 70%, still more preferably by at least about 80%, still more preferably by at least about 90%, and still more preferably by at least about 95%.

Effective amounts of the inhibitory compounds described herein capable of significantly reducing the production of TSST-1 are as follows: (1) compounds of Structure (I): from about 0.0001 micromoles/gram absorbent product to about 0.08 micromoles/gram absorbent product, desirably from about 0.0005 micromoles/gram of absorbent product to about 0.05 micromoles/gram of absorbent product; and (2) compounds of Structures (II) and (III): from about 0.05 micromoles/gram of absorbent product to 5 micromoles/gram of absorbent product, desirably from about 0.1 micromoles/gram of absorbent product to about 1 micromole/gram of absorbent product. Specifically, effective amounts of hexachlorophene include 0.00024 micromoles/gram of absorbent product to about 0.08 micromoles/gram of absorbent product, desirably from about 0.001 micromoles/gram of absorbent product to about 0.05 micromoles/gram of absorbent product. Specifically, effective amounts of triclosan include from about 0.0005 micromoles/gram of absorbent product to about 0.03 micromoles/gram of absorbent product. Specifically, effective amounts of cerulenin include from about 0.1 micromoles/gram of absorbent product to about 1 micromole/gram of absorbent product.

Although discussed in the singular, one skilled in the art would recognize that two or more of the inhibitory compounds can be combined in an absorbent article. In such embodiments, it may be possible to reduce the amount of the inhibitory compounds incorporated into the absorbent article and still achieve satisfactory results.

The inhibitory compounds used in the practice of the present invention can be prepared and applied to the absorbent article in any suitable form, but are preferably prepared in forms including, without limitation, aqueous solutions, lotions, balms, gels, salves, ointments, boluses, suppositories, and the like. The inhibitory compounds may be applied to the absorbent article using conventional methods. For example, unitary tampons without separate wrappers may be dipped directly into a liquid bath containing the inhibitory compound and then can be air dried, if necessary, to remove any volatile solvents. For compressed tampons, impregnating any of its elements is best done before compressing. The inhibitory compounds when incorporated on and/or into the absorbent materials may be fugitive, loosely adhered, bound, or any combination thereof. As used herein, the term "fugitive" means that the composition is capable of migrating through the absorbent material.

It is not necessary to impregnate the entire absorbent body of the tampon or other absorbent article with the inhibitory compound. Optimum results both economically and functionally can be obtained by concentrating the material on or near the outer surface where it may be most effective in inhibiting the formation of TSST-1 during use.

The inhibitory compounds as described herein may be employed with one or more conventional pharmaceutically-acceptable and compatible carrier materials useful for the desired application. The carrier can be capable of co-dissolving or suspending the compound applied to the absorbent article. Carrier materials suitable for use in the instant invention include those well-known for use in the cosmetic and medical arts as a basis for ointments, lotions, creams, salves, aerosols, suppositories, gels, and the like.

The absorbent articles of the present invention may additionally include adjunct components conventionally found in pharmaceutical compositions in their art-established fashion and at their art-established levels. For example, the absorbent articles may contain additional compatible pharmaceutically active materials for combination therapy, such as supplementary antimicrobial, antioxidants, anti-parasitic agents, antipruritics, astringents, local anaesthetics, or anti-inflammatory agents.

In another embodiment of the present invention, the inhibitory compounds of Structures (I), (II), and/or (III) above are incorporated into or onto an absorbent article in combination with one or more compounds known to retard TSST-1 production without significantly eliminating the beneficial bacterial flora. These include, for example, aromatic compounds, isoprenoid compounds, compounds with an ether, ester, amide, glycosidic, or amine bond linking a $C_8$–$C_{18}$ fatty acid to an aliphatic alcohol, polyalkoxylated sulfate salt, or polyalkoxylated sulfosuccinic salt.

In one embodiment, the compounds of Structures (I), (II), and/or (III) above are used in combination with aromatic compounds having the following chemical structure:

$$\text{(IV)}$$

[benzene ring with substituents $R^1$, $R^2$, $R^3$, $R^4$]

wherein $R^1$ is selected from the group consisting of $$-\overset{\overset{O}{\|}}{C}OR^5$$

hydrogen, $-OR^5$, $-R^6C(O)H$, $-R^6OH$, $-R^6COOH$, $-OR^6OH$, $-OR^6COOH$, $-C(O)NH_2$, $$-(NC(O)R^5) \quad -(R^7OH) \quad -(R^7COOH)$$
(with H, $NH_2$, $NH_2$ substituents respectively)

$$-(R^7OH) \quad -(R^7COOH)$$
(with $NHR^8$, $NHR^8$ substituents respectively)

and $NH_2$ and salts thereof; $R^5$ is a monovalent saturated or unsaturated aliphatic hydrocarbyl moiety; $R^6$ is a divalent saturated or unsaturated aliphatic hydrocarbyl moiety; $R^7$ is a trivalent saturated or unsaturated aliphatic hydrocarbyl moiety; $R^8$ is hydrogen or a monovalent substituted or unsubstituted saturated or unsaturated aliphatic hydrocarbyl moiety which may or may not be interrupted with hetero atoms; $R^2$, $R^3$, and $R^4$ are independently selected from the group consisting of —H, —OH, C(O)OH, and —C(O)$R^9$; and $R^9$ is a monovalent saturated or unsaturated aliphatic hydrocarbyl moiety.

With respect to the aromatic compounds of Structure (IV), the hydrocarbyl moieties include both straight chain and branched chain hydrocarbyl moieties and may or may not be substituted and/or interrupted with hetero atoms. Desirably, the aromatic compounds for use in the present invention contain at least one —OH and/or —C(O)OH group. The —OH and/or —C(O)OH group can be bonded to the aromatic structure, or can be bonded to an atom which may or may not be directly bonded to the aromatic structure. $R^5$ is desirably a monovalent saturated aliphatic hydrocarbyl moiety having from 1 to about 15 carbon atoms, preferably from 1 to about 14 carbon atoms. $R^6$ is desirably a divalent saturated or unsaturated aliphatic hydrocarbyl moiety having from 1 to about 15 carbon atoms, preferably from 1 to about 14 carbon atoms. $R^7$ is desirably a trivalent saturated or unsaturated aliphatic hydrocarbyl moiety having from 1 to about 15 carbon atoms, preferably from 1 to about 10 carbon atoms, and more preferably from 1 to about 4 carbon atoms. Hetero atoms which can interrupt the hydrocarbyl moiety include, for example, oxygen and sulfur.

Preferred aromatic compounds used in combination with the inhibitory compounds of Structures (I), (II), and/or (III) include 2-phenylethanol, benzyl alcohol, trans-cinnamic acid, methyl ester of 4-hydroxybenzoic acid, 2-hydroxybenzoic acid, 2-hydoxybenzamide, acetyl tyrosine, 3,4,5-trihydroxybenzoic acid, lauryl 3,4,5-trihydroxybenzoate, phenoxyethanol, 4-hydroxy-3-methoxybenzoic acid, p-aminobenzoic acid, and 4-acetamidophenol.

The absorbent articles of the present invention containing a first inhibitory compound of Structure (I), (II), and/or (III) combined with a second inhibitory aromatic compound of Structure (IV) contain a sufficient amount of both inhibitory compounds to substantially inhibit the formation of TSST-1 when the absorbent article is exposed to *S. aureus* bacteria. Preferably, the combination of inhibitory compounds reduces the formation of TSST-1 when the absorbent article is exposed to *S. aureus* by at least about 40%, more preferably by at least about 50%, still more preferably by at least about 60%, still more preferably by at least about 70%, still more preferably by at least about 80%, still more preferably by at least about 90%, and still more preferably by at least about 95%.

Generally, the amount of the aromatic compound included in the absorbent article is at least about 0.1 micromoles of aromatic compound per gram of absorbent article, and desirably at least about 0.5 micromoles of aromatic compound per gram of absorbent article to 100 micromoles of aromatic compound per gram of absorbent article. In a preferred embodiment, the absorbent article contains from about 1.0 micromole of aromatic compound per gram of absorbent article to about 50 micromoles of aromatic compound per gram of absorbent article. The amount of first inhibitory compound of Structure (I), (II), and/or (III) is as described above.

In another embodiment, the inhibitory compounds of Structures (I), (II), and/or (III) are combined with isoprenoid compounds in the absorbent article. As used herein, the term "isoprenoid compound" means a hydrocarbon containing compound structurally based on multiple isoprene units, which may or may not be substituted, and may or may not contain hetero atoms and functional groups such as carbonyl (e.g., ketones and aldehydes), and hydroxy (e.g., alcohols). Isoprene, also commonly referred to as 2-methyl-1,3-butadiene, has the following chemical structure:

$$\underset{H}{\overset{H}{>}}C=\underset{H}{\overset{CH_3}{C}}-\underset{H}{\overset{H}{C}}=C\underset{H}{\overset{H}{<}} \quad (V)$$

Desirably, the isoprenoid compounds used in the accordance with the present invention are terpene compounds. As used herein, "terpene compound" refers to compounds which are based on isoprene, but which may contain heteroatoms such as oxygen and/or hydroxyls (e.g., alcohols), or carbonyl (e.g., aldehydes and ketones) functionalities.

Various types of terpenes are useful in accordance with the present invention. The terpene compounds may be cyclic or acyclic, and may be saturated or unsaturated. Suitable terpene compounds include hemiterpenes (terpenes containing 5 carbon atoms), monoterpenes (terpenes containing 10 carbon atoms), sesquiterpenes (terpenes containing 15 carbon atoms), diterpenes (terpenes containing 20 carbon atoms), triterpenes (terpenes containing 30 carbon atoms), tetraterpenes (terpenes containing 40 carbon atoms), as well as polyterpenes and mixtures and combinations thereof. Terpenoids, oxygenated derivatives of terpenes, which may or may not contain hydroxyl and/or carbonyl groups, are also suitable terpene compounds. Examples of monoterpenes useful in the present invention include α-pinen, β-pinen, campher, geraniol, borneol, nerol, thujone, citral a, limonen, cineole, terpineol, terpinene, terpin (cis and trans), α-myrcene, β-myrcene, dipentene, linalool, 2-methyl-6-methylene-1,7-octadiene, and menthol. Examples of sesquiterpenes useful in the present invention include, humulene, ionone, nerolidol and farnesol. An example of a suitable diterpene is phytol. A suitable triterpene for use in the present invention is squalen. Suitable tetraterpenes for use in the present invention include α-carotene, β-carotene, γ carotene, δ-carotene, lutein, and violaxanthin.

Preferred isoprenoid compounds for use in the present invention include terpineol, β-ionone, terpin (cis and trans), linalool, geraniol, menthol and mixtures and combinations thereof.

The absorbent articles of the present invention containing a first inhibitory compound of Structure (I), (II), and/or (III) combined with a second inhibitory isoprenoid compound of Structure (V) contain a sufficient amount of both inhibitory compounds to substantially inhibit the formation of TSST-1 when the absorbent article is exposed to *S. aureus* bacteria. Preferably, the combination of inhibitory compounds reduces the formation of TSST-1 when the absorbent article is exposed to *S. aureus* by at least about 40%, more preferably by at least about 50%, still more preferably by at least about 60%, still more preferably by at least about 70%, still more preferably by at least about 80%, still more preferably by at least about 90%, and still more preferably by at least about 95%.

Generally, the amount of the isoprenoid compound included in the absorbent article is at least about 0.1 micromoles of isoprenoid compound per gram of absorbent article, and desirably from about 0.5 micromoles of isoprenoid compound per gram of absorbent article to about 100 micromoles of isoprenoid compound per gram of absorbent article. In a preferred embodiment, the absorbent article contains from about 1 micromole of isoprenoid compound per gram of absorbent article to about 50 micromoles of isoprenoid compound per gram of absorbent article. The amount of first inhibitory compound of Structure (I), (II), and/or (III) is as described above.

In another embodiment, the inhibitory compounds of Structures (I), (II), and/or (III) are combined with certain ether compounds in the absorbent article. The ether compound has the following chemical structure:

$$R^{10}—O—R^{11} \quad\quad (VI)$$

wherein $R^{10}$ is a straight or branched alkyl or alkenyl group having a chain of from about 8 to about 18 carbon atoms and $R^{11}$ is selected from an alcohol, a polyalkoxylated sulfate salt or a polyalkoxylated sulfosuccinate salt.

The alkyl, or the $R^{10}$ moiety of the ether compounds useful in the practice of the present invention, can be obtained from saturated and unsaturated fatty acid compounds. Suitable compounds include, $C_8$–$C_{18}$ fatty acids, and preferably, fatty acids include, without limitation, caprylic, capric, lauric, myristic, palmitic and stearic acid whose carbon chain lengths are 8, 10, 12, 14, 16, and 18, respectively. Highly preferred materials include capric, lauric, and myristic acids.

Preferred unsaturated fatty acids are those having one or two cis-type double bonds and mixtures of these materials. Suitable materials include myrystoleic, palmitoleic, linolenic and mixtures thereof.

Desirably, the $R^{11}$ moiety is an aliphatic alcohol which can be ethoxylated or propoxylated for use in the ether compositions in combination with the inhibitory agents of Structures (I), (II), and/or (III). Suitable aliphatic alcohols include glycerol, sucrose, glucose, sorbitol and sorbitan. Preferred ethoxylated and propoxylated alcohols include glycols such as ethylene glycol, propylene glycol, polyethylene glycol and polypropylene glycol.

The aliphatic alcohols can be ethoxylated or propoxylated by conventional ethoxylating or propoxylating compounds and techniques. The compounds are preferably selected from the group consisting of ethylene oxide, propylene oxide, and mixtures thereof, and similar ringed compounds which provide a material which is effective.

The $R^{11}$ moiety can further include polyalkoxylated sulfate and polyalkoxylated sulfosuccinate salts. The salts can have one or more cations. Preferably, the cations are sodium, potassium or both.

Preferred ether compounds for use in combination with the inhibitory compounds of Structures (I), (II), and/or (III) include laureth-3, laureth-4, laureth-5, PPG-5 lauryl ether, 1-0-dodecyl-rac-glycerol, sodium laureth sulfate, potassium laureth sulfate, disodium laureth (3) sulfosuccinate, dipotassium laureth (3) sulfosuccinate, and polyethylene oxide (2) sorbitol ether.

The absorbent articles of the present invention containing a first inhibitory compound of Structure (I), (II), and/or (III) combined with a second inhibitory ether compound or Structure (VI) contain a sufficient amount of both inhibitory compounds to substantially inhibit the formation of TSST-1 when the absorbent article is exposed to *S. aureus* bacteria. Preferably, the combination of inhibitory compounds reduces the formation of TSST-1 when the absorbent article is exposed to *S. aureus* by at least about 40%, more preferably by at least about 50%, still more preferably by at least about 60%, still more preferably by at least about 70%, still more preferably by at least about 80%, still more preferably by at least about 90%, and still more preferably by at least about 95%.

Generally, the amount of ether compound included in the absorbent article is at least about 0.1 micromoles of ether compound per gram of absorbent article, and desirably at least about 0.005 millimoles of ether compound per gram of absorbent article. In a preferred embodiment, the absorbent article contains from about 5.0 micromoles of ether compound per gram of absorbent article to about 2 millimoles of ether compound per gram of absorbent article. The amount of first inhibitory compound of Structure (I), (II), and/or (III) is as described above.

In another embodiment, the inhibitory compounds of Structures (I), (II), and/or (III) can be used in combination with an alkyl polyglycoside compound in the absorbent article. Suitable alkyl polyglycosides for use in combination with the inhibitory compounds of Structures (I), (II), and /or (III) include alkyl polyglycosides having the following chemical structure:

$$H—(Z_n)—O—R^{14} \quad\quad (VII)$$

wherein Z is a saccharide residue having 5 or 6 carbon atoms, n is a whole number from 1 to 6, and $R^{14}$ is a linear or branched alkyl group having from about 8 to about 18 carbon atoms. Commercially available examples of suitable alkyl polyglycosides having differing carbon chain lengths include Glucopon 220, 225, 425, 600, and 625, all available from Henkel Corporation (Ambler, Pa.). These products are all mixtures of alkyl mono- and oligoglucopyranosides with differing alkyl group chain lengths based on fatty alcohols derived from coconut and/or palm kernel oil. Glucopon 220, 225, and 425 are examples of particularly suitable alkyl polyglycosides for use in combination with the inhibitory compounds of Structures (I), (II), and/or (III). Another example of a suitable commercially available alkyl polyglycoside is TL 2141, a Glucopon 220 analog available from ICI Surfactants (Wilmington, Del.).

It should be understood that as referred to herein, an alkyl polyglycoside may consist of a single type of alkyl polyglycoside molecule or, as is typically the case, may include a mixture of different alkyl polyglycoside molecules. The different alkyl polyglycoside molecules may be isomeric and/or may be alkyl polyglycoside molecules with differing alkyl groups and/or saccharide portions. By use of the term alkyl poyglycoside isomers reference is made to alkyl polyglycosides which, although including the same alkyl ether residues, may vary with respect to the location of the alkyl ether residue in the alkyl polyglycoside as well as isomers which differ with respect to the orientation of the functional groups about one or more chiral centers in the molecules. For example, an alkyl polyglycoside can include a mixture of molecules with saccharide portions which are mono, di-, or oligosaccharides derived from more than one 6 carbon saccharide residue and where the mono-, di- or oligosaccharide has been etherified by reaction with a mixture of fatty alcohols of varying carbon chain length. The present alkyl polyglycosides desirably include alkyl groups where the average number of carbon atoms in the alkyl chain is about 8 to about 14 or from about 8 to about 12. One example of a suitable alkyl polyglycoside is a mixture of alkyl polyglycoside molecules with alkyl chains having from about 8 to about 10 carbon atoms.

The alkyl polyglycosides employed in the absorbent articles in combination with the inhibiting compounds described herein can be characterized in terms of their hydrophilic lipophilic balance (HLB). This can be calculated based on their chemical structure using techniques well known to those skilled in the art. The HLB of the alkyl polyglycosides used in the present invention typically falls within the range of about 10 to about 15. Desirably, the present alkyl polyglycosides have an HLB of at least about 12 and, more desirably, about 12 to about 14.

The absorbent articles of the present invention containing a first inhibitory compound of Structure (I), (II), and/or (III) and a second inhibitory alkyl polyglycoside compound of Structure (VII) contain a sufficient amount of both inhibitory compounds to substantially inhibit the formation of TSST-1 when the absorbent article is exposed to S. aureus bacteria. Preferably, the combination of inhibitory compounds reduces the formation of TSST-1 when the absorbent article is exposed to S. aureus by at least about 40%, more preferably by at least about 50%, still more preferably by at least about 60%, still more preferably by at least about 70%, still more preferably by at least about 80%, still more preferably by at least about 90%, and still more preferably by at least about 95%.

Generally, the amount of alkyl polyglycoside compound included in the absorbent article is at least about 0.0001 millimoles of alkyl polyglycoside per gram of absorbent article, and preferably at least about 0.005 millimoles of alkyl polyglycoside per gram of absorbent article. In a preferred embodiment, the absorbent article contains from about 0.005 millimoles per gram of absorbent article to about 1 millimole per gram of absorbent article of alkyl polyglycoside. The amount of first inhibitory compound of Structure (I), (II), and/or (III) is as described above.

In another embodiment, the inhibitory compounds of Structures (I), (II), and/or (III) are combined with an amide containing compound having the following chemical structure:

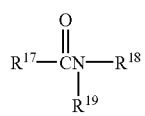

(VIII)

wherein $R^{17}$, inclusive of the carbonyl carbon, is an alkyl group having 8 to 18 carbon atoms, and $R^{18}$ and $R^{19}$ are independently selected from hydrogen or an alkyl group having from 1 to about 12 carbon atoms which may or may not be substituted with groups selected from ester groups, ether groups, amine groups, hydroxyl groups, carboxyl groups, carboxyl salts, sulfonate groups, sulfonate salts, and mixtures thereof.

$R^{17}$ can be derived from saturated and unsaturated fatty acid compounds. Suitable compounds include, $C_8$–$C_{18}$ fatty acids, and preferably, the fatty acids include, without limitation, caprylic, capric, lauric, myristic, palmitic and stearic acid whose carbon chain lengths are 8, 10, 12, 14, 16, and 18, respectively. Highly preferred materials include capric, lauric, and myristic.

Preferred unsaturated fatty acids are those having one or two cis-type double bonds and mixtures of these materials. Suitable materials include myrystoleic, palmitoleic, linolenic and mixtures thereof.

The $R^{18}$ and $R^{19}$ moieties can be the same or different and each being selected from hydrogen and an alkyl group having a carbon chain having from 1 to about 12 carbon atoms. The $R^{18}$ and $R^{19}$ alkyl groups can be straight or branched and can be saturated or unsaturated. When $R^{18}$ and/or $R^{19}$ are an alkyl moiety having a carbon chain of at least 2 carbons, the alkyl group can include one or more substituent groups selected from ester, ether, amine, hydroxyl, carboxyl, carboxyl salts, sulfonate and sulfonate salts. The salts can have one or more cations selected from sodium, potassium or both.

Preferred amide compounds for use in combination with the inhibitory compounds of Structures (I), (II), and/or (III) include sodium lauryl sarcosinate, lauramide monoethanolamide, lauramide diethanolamide, lauramidopropyl dimethylamine, disodium lauramido monoethanolamide sulfosuccinate and disodium lauroamphodiacetate.

The absorbent articles of the present invention containing a first inhibitory compound of Structure (I), (II), and/or (III) and a second inhibitory amide-containing compound of Structure (VIII) contain a sufficient amount of both inhibitory compounds to substantially inhibit the formation of TSST-1 when the absorbent article is exposed to S. aureus bacteria. Preferably, the combination of inhibitory compounds reduces the formation of TSST-1 when the absorbent article is exposed to S. aureus by at least about 40%, more preferably by at least about 50%, still more preferably by at least about 60%, still more preferably by at least about 70%, still more preferably by at least about 80%, still more preferably by at least about 90%, and still more preferably by at least about 95%.

In accordance with the present invention, the absorbent article contains an effective amount of the combination of the inhibitory compounds described herein and amide-containing compounds. The amount of amide-containing compound included in the absorbent article is at least about 0.0001 millimoles of amide-containing compound per gram of absorbent article, and preferably at least about 0.005 millimoles of amide-containing compound per gram of absorbent article. In a preferred embodiment, the absorbent article contains from about 0.005 millimoles per gram of absorbent article to about 2 millimoles per gram of absorbent article. The amount of first inhibitory compound of Structure (I), (II), and/or (III) is as described above.

In another embodiment, the inhibitory compounds of Structures (I), (II), and/or (III) are combined in the absorbent article with an amine compound having the following chemical structure:

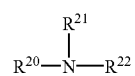

(IX)

wherein $R^{20}$ is an alkyl group having from about 8 to about 18 carbon atoms and $R^{21}$ and $R^{22}$ are independently selected from the group consisting of hydrogen and alkyl groups having from 1 to about 18 carbon atoms and which can have one or more substitutional moieties selected from the group consisting of hydroxyl, carboxyl, carboxyl salts and imidazoline. The combination of compounds of Structures (I), (II), and/or (III) and the amine compounds of Structure (IX) are effective in substantially inhibiting the production of TSST-1 from Gram positive bacteria.

Desirably, $R^{20}$ is derived from fatty acid compounds which include, without limitation, caprylic, capric, lauric, myristic, palmitic and stearic acid whose carbon chain lengths are 8, 10, 12, 14, 16, and 18, respectively. Highly preferred materials include capric, lauric, and myristic. Preferred unsaturated fatty acids are those having one or two cis-type double bonds and mixtures of these materials. Suitable materials include myrystoleic, palmitoleic, linolenic, and mixtures thereof.

The $R^{21}$ and $R^{22}$ alkyl groups can further include one or more substitutional moieties selected from hydroxyl, carboxyl, carboxyl salts, and $R^1$ and $R^2$ can form an unsaturated heterocyclic ring that contains a nitrogen that connects via a double bond to the alpha carbon of the $R^1$ moiety to form a substituted imidazoline. The carboxyl salts can have one or more cations selected from sodium potassium or both. The $R^{20}$, $R^{21}$, and $R^{22}$ alkyl groups can be straight or branched and can be saturated or unsaturated.

Preferred amine compounds for use with the inhibitory compounds of Structures (I), (II), and/or (III) include triethanolamide laureth sulfate, lauramine, lauramino propionic acid, sodium lauriminodipropionic acid, lauryl hydroxyethyl imidazonline and mixtures thereof.

In another embodiment, the amine compound can be an amine salt having the following chemical structure:

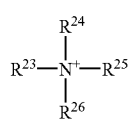

(X)

wherein $R^{23}$ is an anionic moiety associated with the amine and is derived from an alkyl group having from about 8 to about 18 carbon atoms, and $R^{24}$, $R^{25}$, and $R^{26}$ are independently selected from the group consisting of hydrogen and alkyl group having from 1 to about 18 carbon atoms and which can have one or more substitutional moieties selected from the group consisting of hydroxyl, carboxyl, carboxyl salts, and imidazoline. $R^{24}$, $R^{25}$, and $R^{26}$ can be saturated or unsaturated. Desirably, $R^{23}$ is a polyalkyloxylated alkyl sulfate. A preferred compound illustrative of an amine salt is TEA laureth sulfate.

The absorbent articles of the present invention containing a first inhibitory compound of Structure (I), (II), and/or (III) and a second inhibitory amine and/or amine salt compound contain a sufficient amount of both inhibitory compounds to substantially inhibit the formation of TSST-1 when the absorbent article is exposed to S. aureus bacteria. Preferably, the combination of inhibitory compounds reduces the formation of TSST-1 when the absorbent article is exposed to *S. aureus* by at least about 40%, more preferably by at least about 50%, still more preferably by at least about 60%, still more preferably by at least about 70%, still more preferably by at least about 80%, still more preferably by at least about 90%, and still more preferably by at least about 95%.

Generally, the amount of amine and/or amine salt compound included in the absorbent article is at least about 0.00001 millimoles of amine and/or amine salt per gram of absorbent article, and preferably at least about 0.0005 millimoles of amine and/or amine salt per gram of absorbent article. In a preferred embodiment, the absorbent article contains from about 0.005 millimoles per gram of absorbent article to about 2 millimoles per gram of absorbent article. The amount of first inhibitory compound of Structure (I), (II), and/or (III) is as described above.

The present invention is illustrated by the following examples which are merely for the purpose of illustration and are not to be regarded as limiting the scope of the invention or manner in which it may be practiced.

EXAMPLE 1

In this Example, the effect of various test compounds on the growth of *S. aureus* and the production of TSST-1 was determined. The test compound, in the desired concentration (expressed in micrograms/milliliter) was placed in 10 mL of a growth medium in a sterile, 50 mL conical polypropylene tube (Sarstedt, Inc. Newton, N.C.).

The growth medium was prepared by dissolving 37 grams of brain heart infusion broth (BHI) (Difco Laboratories, Cockeysville, Md.) in 880 mL of distilled water and sterilizing the broth according to the manufacturer's instructions. The BHI was supplemented with fetal bovine serum (FBS) (100 mL) (Sigma Chemical Company, St. Louis, Mo.). Hexahydrate of magnesium chloride (0.021 M, 10 mL) (Sigma Chemical Company, St. Louis, Mo.) was added to the BHI-FBS mixture. Finally, L-glutamine (0.027 M, 10 mL) (Sigma Chemical Company, St. Louis, Mo.) was added to the mixture.

Compounds to be tested included hexachlorophene, triclosan and 4-hydroxydiphenyl methane. Test compounds were received as solids. The solids were dissolved in methanol, spectrophotometric grade (Sigma Chemical Company, St. Louis, Mo.) at a concentration that permitted the addition of 200 microliters of the solution to 10 mL of growth medium for the highest concentration tested. Each test compound that was dissolved in methanol was added to the growth medium in the amount necessary to obtain the desired final concentration.

In preparation for inoculation of the tubes of growth medium containing the test compounds, an inoculating broth was prepared as follows: *S. aureus* (MN8) was streaked onto a tryptic soy agar plate (TSA; Difco Laboratories Cockeysville, Md.) and incubated at 35° C. The test organism was obtained from Dr. Pat Schlievert, Department of Microbiology, University of Minnesota Medical School, Minneapolis, Minn. After 24 hours of incubation three to five individual colonies were picked with a sterile inoculating loop and used to inoculate 10 mL of growth medium. The tube of inoculated growth medium was incubated at 35° C. in atmospheric air. After 24 hours of incubation, the culture was removed from the incubator and mixed well on a S/P brand vortex mixer. A second tube containing 10 mL of the growth medium was inoculated with 0.5 mL of the above-described 24 hour old culture and incubated at 35° C. in atmospheric air. After 24 hours of incubation the culture was removed from the incubator and mixed well on a S/P brand vortex mixer. The optical density of the culture fluid was determined in a microplate reader (Bio-Tek Instruments, Model EL309, Winooski, Vt.). The amount of inoculum necessary to give $5\times10^6$ CFU/mL in 10 mL of growth medium was determined using a standard curve.

This Example included tubes of growth medium with varying concentrations of test compounds, tubes of growth medium without test compounds (control) and tubes of growth medium with 20–400 microliters of methanol (control). Each tube was inoculated with the amount of inoculum determined as described above. The tubes were capped with foam plugs (Identi-plug plastic foam plugs, Jaece Industries purchased from VWR Scientific Products, South Plainfield, N.J.). The tubes were incubated at 35° C. in atmospheric air containing 5% by volume $CO_2$. After 24 hours of incubation the tubes were removed from the incubator and the optical density (600 nm) of the culture fluid was determined and the culture fluid was assayed for the number of colony forming units (CFU) of *S. aureus* using standard plate count procedures. The remaining culture fluid was prepared for the analysis of TSST-1 as follows: the culture fluid was centrifuged at 2500 rpm at about 2–10° C. for 15 minutes. The supernatant was filter sterilized through an Autovial 5 syringeless filter, 0.2 micrometer pore size (Whatman, Inc., Clifton N.J.). The resulting fluid was frozen at −70° C. in a Fisherbrand 12×75 milliliter polystyrene culture tube.

The amount of TSST-1 per mL was determined by a non-competitive, sandwich enzyme-linked immunoabsorbent assay (ELISA). Samples of the culture fluid and the TSST-1 reference standard were assayed in triplicate. The method employed was as follows: four reagents, TSST-1 (#TT-606), rabbit polyclonal anti-TSST-1 IgG (LTI-101), rabbit polyclonal anti-TSST-1 IgG conjugated to horseradish peroxidase (LTC-101), and normal rabbit serum (NRS) certified anti-TSST-1 free (NRS-10) were purchased from Toxin Technology (Sarasota, Fla.). A 10 microgram/milliliter solution of the polyclonal rabbit anti-TSST-1 IgG was prepared in phosphate buffered saline (PBS) (pH 7.4). The PBS was prepared from 0.016 molar $NaH_2PO_4$, 0.004 molar $NaH_2PO_4$—$H_2O$, 0.003 molar KCl and 0.137 molar NaCl, (Sigma Chemical Company, St. Louis, Mo.). One hundred microliters of the polyclonal rabbit anti-TSST-1 IgG solution was pipetted into the inner wells of polystyrene microplates (Nunc-Denmark, Catalogue Number 439454). The plates were covered and incubated at room temperature overnight. Unbound anti-toxin was removed by draining until dry. TSST-1 was diluted to 10 nanograms/milliliter in PBS with phosphate buffered saline (pH 7.4) containing 0.05% (vol/vol) Tween-20 (PBS-Tween) (Sigma Chemical Company, St. Louis, Mo.) and 1% NRS (vol/vol) and incubated at 4° C. overnight. Test samples were combined with 1% NRS (vol/vol) and incubated at 4° C. overnight.

The plates were treated with 100 microliters of a 1% (wt/vol) solution of the sodium salt of casein in PBS (Sigma Chemical Company, St. Louis, Mo.), covered and incubated at 35° C. for one hour. Unbound BSA was removed by 3 washes with PBS-Tween. TSST-1 reference standard (10 nanograms/milliliter) treated with NRS, test samples treated with NRS, and reagent controls were pipetted in 200 microliter volumes to their respective wells on the first and seventh columns of the plate. One hundred microliters of PBS-Tween was added to the remaining wells. The TSST-1 reference standard and test samples were then serially diluted 6 times in the PBS-Tween by transferring 100 microliters from well-to-well. The samples were mixed prior to transfer by repeated aspiration and expression. This was followed by incubation for 1.5 hours at 35° C. and five washes with PBS-T and three washes with distilled water to remove unbound toxin.

The rabbit polyclonal anti-TSST-1 IgG conjugated to horseradish peroxidase wash diluted according to manufacturer's instructions and 50 microliters was added to each microtiter well, except well A-1, the conjugate control well. The plates were covered and incubated at 35° C. for one hour.

Following incubation the plates were washed five times in PBS-Tween and three times with distilled water. Following the washes, the wells were treated with 100 microliters of horseradish peroxidase substrate buffer consisting of 5 milligrams of o-phenylenediamine and 5 microliters of 30% hydrogen peroxide in 11 mL of citrate buffer (pH 5.5). The citrate buffer was prepared from 0.012 M anhydrous citric acid and 0.026 M dibasic sodium phosphate. The plates were incubated for 15 minutes at 35° C. The reaction was stopped by the addition of 50 microliters of a 5% sulfuric acid solution. The intensity of the color reaction in each well was evaluated using the BioTek Model EL309 microplate reader (OD 490 nanometers). TSST-1 concentrations in the test samples were determined from the reference toxin regression equation derived during each assay procedure. The efficacy of the compounds in inhibiting the production of TSST-1 is shown in Table I below.

In accordance with the present invention, the data in Table 1 shows that *S. aureus* (MN8), when compared to the control, produced significantly less TSST-1 in the presence of the hexachlorophene and triclosan compounds. At the concentration tested, these compounds reduced the amount of toxin produce by 68% to 88%. Although 4-hydroxydiphenyl-methane did reduce the toxin production by about 24%, it lacks the chlorine and hydroxyl groups that have been shown to stabilize triclosan in the active site of the enzyme/NAD complex.

TABLE 1

| Compound | Amount Test Compound | Optical Density 600 nm | CFU/mL | ELISA: TSST-1 ng/OD unit | Reduction of Toxin (%) |
|---|---|---|---|---|---|
| Methanol | 200 μL | 0.569 | 2.9E+08 | 1038 | N/A |
| Hexa-chlorophene | 2 μg/mL | 0.350 | 3.7E+08 | 330 | 68% |
| Triclosan | 0.01 μg/mL | 0.271 | 1.0E+08 | 129 | 88% |
| 4-Hydroxy-diphenyl-methane | 2 μg/mL | 0.581 | 1.1E+08 | 785 | 24% |

N/A = Not Applicable

EXAMPLE 2

In this Example, the growth of, and TSST-1 production by, *S. aureus* FRI-1169 and 3 mutants able to grow in the presence of triclosan, was evaluated. *S. aureus* FRI-1169 was obtained as a lyophilized culture from the stock collection of Merlin Bergdoll (Food Research Institute, Madison Wis.). The mutants were selected by plating overnight growth of *S. aureus* FRI-1169 in growth medium onto tryptic soy agar plates containing 5 micrograms/milliliter triclosan. The effect of triclosan was determined by placing a range of concentrations, expressed in micrograms/milliliter, in 10 mL of growth medium as set forth in Example 1. The samples were then tested and evaluated utilizing the procedure set forth in Example 1. The effect of the triclosan on the growth of *S. aureus* FRI-1169 and on the production of TSST-1 is shown in Table 2.

In accordance with the present invention, the data shows that *S. aureus* FRI-1169, when compared to the control, produced less TSST-1 in the presence of triclosan. In addition, mutants selected for their ability to grow in the presence of triclosan showed a reduction in toxin production, compared to the parent strain, of 71%–95% in the presence of triclosan.

TABLE 2

| Compound | Amount Test Compound | Optical Density 600 nm | CFU/mL | ELISA: TSST-1 ng/OD unit | Reduction of Toxin % |
|---|---|---|---|---|---|
| Methanol | 200 μL | 0.577 | 1.79E+09 | 958 | N/A |
| Triclosan | 0.5 μg/mL | 0.625 | 1.50E+09 | 40 | 96% |

TABLE 2-continued

| Compound | Amount Test Compound | Optical Density 600 nm | CFU/mL | ELISA: TSST-1 ng/OD unit | Reduction of Toxin % |
|---|---|---|---|---|---|
| Mutant #1 | 5 µg/mL | 0.530 | 1.78E+09 | 47 | 95% |
| Mutant #2 | 5 µg/mL | 0.464 | 1.41E+09 | 114 | 88% |
| Mutant #3 | 5 µg/mL | 0.514 | 1.58E+09 | 282 | 71% |

N/A = Not Applicable

EXAMPLE 3

In this Example, the growth of, and TSST-1 production by, S. aureus FRI-1187 and 3 mutants able to grow in the presence of triclosan were evaluated. S. aureus FRI-1187 was obtained as a lyophilized culture from the stock collection of Merlin Bergdoll (Food Research Institute, Madison Wis.). The mutants were selected by plating overnight growth of S. aureus FRI-1187 in growth medium onto tryptic soy agar plates containing 5 microgram/milliliter triclosan. The effect of triclosan was determined by placing a range of concentrations, expressed in microgram/milliliter, in 10 mL of a growth medium as in Example 1. The samples were then tested and evaluated as in Example 1. The effect of the triclosan on the growth of S. aureus FRI-1187 and mutants and on the production of TSST-1 is shown in Table 3 below.

In accordance with the present invention, Table 3 shows that S. aureus FRI-1187, when compared to the control, produced less TSST-1 in the presence of triclosan. In addition, mutants selected for their ability to grow in the presence of triclosan showed a reduction in toxin production, compared to the parent strain, of 85%–94% in the presence of triclosan.

TABLE 3

| Compound | Amount Test Compound | Optical Density 600 nm | CFU/mL | ELISA: TSST-1 ng/OD unit | Reduction of Toxin % |
|---|---|---|---|---|---|
| Methanol | 200 uL | 0.594 | 4.40E+09 | 675 | N/A |
| Triclosan | 0.5 ug/mL | 0.156 | 1.56E+09 | 95 | 86% |
| Mutant #4 | 10 ug/mL | 0.613 | Not Determined | 102 | 85% |
| Mutant #5 | 10 ug/mL | 0.618 | Not Determined | 42 | 94% |
| Mutant #6 | 10 ug/mL | 0.613 | 1.41E+09 | 42 | 94% |

N/A = Not Applicable

EXAMPLE 4

In this Example, an experiment was conducted to evaluate the growth of, and TSST-1 production by, S. aureus in the presence of cerulenin. The effect of the test compounds was determined by placing the desired concentration, expressed in micrograms/milliliter, in 10 mL of a growth medium as set forth in Example 1. The compounds were then tested and evaluated as in Example 1. The effect of the test compounds on the growth of S. aureus MN8 and the production of TSST-1 is shown in Table 4.

In accordance with the present invention, the data in Table 4 show that S. aureus MN8, when compared to the control, produce significantly less TSST-1 in the presence of cerulenin. At the concentrations tested, cerulenin reduced the amount of toxin produced by 89% to 93% on the concentration tested.

TABLE 4

| Compound | Amount Test Compound (ug/mL) | Optical Density 600 nm | CFU/mL | ELISA: TSST-1 ng/OD unit | Reduction of Toxin % |
|---|---|---|---|---|---|
| Methanol | 120 uL | 0.567 | 6.6E+08 | 1088 | N/A |
| Cerulenin | 120 | 0.539 | 3.3E+08 | 123 | 89% |
| Methanol | 80 uL | 0.526 | 3.9E+08 | 1003 | N/A |
| Cerulenin | 80 | 0.626 | 9.1E+08 | 70 | 93% |

N/A = Not Applicable

EXAMPLE 5

In this Example, an experiment was conducted to evaluate the growth of, and TSST-1 production by, S. aureus in the presence of cerulenin. The effect of the test compound was determined by placing the desired concentration, expressed in percent of the active compound, in 100 mL of growth medium (as described in Example 1) in a 500 mL fleaker (Corning Life Sciences, Acton, Mass.). The fleakers were incubated in a 37° C. gyratory waterbath and shaken at 180 rpm. Growth was monitored periodically by optical density (600 nm) readings. When the optical density reached approximately 1.0, samples were taken and prepared for ELISA testing as described in Example 1. The effect of the test compounds on the growth of S. aureus MN8 and on the production of TSST-1 is shown in Table 5 below.

In accordance with the present invention, the data show that S. aureus MN8, when compared to the control, produced significantly less TSST-1 in the presence of cerulenin. At the concentration tested, these compounds reduced the amount of toxin produced by 83% to 95%.

TABLE 5

| Compound | Amount Test Compound | Optical Density 600 nm | ELISA: TSST-1 ng/OD unit | Reduction of Toxin % |
|---|---|---|---|---|
| Growth Medium | 0 | 1.008 (5 hr) | 1653 | N/A |
| Cerulenin | 40 ug/mL | 1.128 (6 hr) | 71 | 95% |
| Cerulenin | 20 ug/mL | 0.956 (5 hr) | 278 | 83% |

N/A = Not Applicable

In view of the above, it will be seen that the several objects of the invention are achieved. As various changes could be made in the above-described absorbent articles without departing from the scope of the invention, it is intended that all matter contained in the above description be interpreted as illustrative and not in a limiting sense.

What is claimed is:

1. A menstrual tampon comprising an absorbent tampon material and an effective amount of a first active ingredient having the general formula:

$$\text{(I)}$$

```
      R_102         R_106
R_100-/=\-R_105-/=\-R_107
      \=/---V'---\=/
R_103-/  \-      /  \-
      R_104        R_108
``` wherein V' is selected from —NH—, —O—, —CH$_2$—, —C(O)OCH$_2$—, —C(O)—, and —C(O)O—, and R$_{100}$, R$_{102}$, R$_{103}$, R$_{104}$, R$_{105}$, R$_{106}$, R$_{107}$ and R$_{108}$ are independently selected from hydrogen, halogen, —OH, —O(R$_{113}$), —SO$_3$Na, —SO$_3$H, —N(R$_{114}$) (R$_{115}$), and —NO$_2$, R$_{113}$ is selected from hydrogen, sodium and a monovalent saturated or unsaturated, substituted or unsubstituted hydrocarbyl moiety having from 1 to 10 carbon atoms which may or may not be interrupted with a heteroatom, and R$_{114}$ and R$_{115}$ are independently selected from hydrogen and a saturated or unsaturated, substituted or unsubstituted hydrocarbyl moiety having from 1 to 10 carbon atoms which may or may not be interrupted with a heteroatom, and the first active ingredient is effective in inhibiting the production of TSST-1 from Gram positive bacteria; and wherein the first active ingredient is present in an amount of from about 0.0001 micromoles/gram of menstrual tampon to about 0.08 micromoles/gram of menstrual tampon.

2. The menstrual tampon as set forth in claim 1 wherein the first active ingredient has the structure of formula (I).

3. The menstrual tampon as set forth in claim 2 wherein the first active ingredient is selected from the group consisting of hexachlorophene, benzylparaben, benzyl salicylate, benzophenone-6, benzophenone-7, benzophenone-8, benzophenone-9, benzophenone-10, benzophenone-12, benzophenone-1, benzophenone-2, benzophenone-3, chlorophene, 2,4-diaminodiphenylamine, dichlorophene, HC Green No. 1, HC Orange No. 1, NH Red No. 1, triclosan, isopropylbenzylsalicylate, and phenyl salicylate.

4. The menstrual tampon as set forth in claim 2 wherein the active ingredient is selected from the group consisting of triclosan and hexachlorophene.

5. The menstrual tampon as set forth in claim 4 wherein the first active ingredient is hexachlorophene and the hexachlorophene is present in an amount of from about 0.00024 micromoles/gram of menstrual tampon to about 0.08 micromoles/gram of menstrual tampon.

6. The menstrual tampon as set forth in claim 4 wherein the first active ingredient is triclosan and the triclosan is present in an amount of from about 0.0005 micromoles/gram of menstrual tampon to about 0.03 micromoles/gram of menstrual tampon.

7. An absorbent article comprising an absorbent material and an effective amount of a first active ingredient having the general formula:

$$\text{(I)}$$

```
      R_102         R_106
R_100-/=\-R_105-/=\-R_107
      \=/---V'---\=/
R_103-/  \-      /  \-
      R_104        R_108
``` wherein V' is selected from —NH—, —O—, —CH$_2$—, —C(O)OCH$_2$—, —C(O)—, and —C(O)O—, R$_{100}$, R$_{102}$, R$_{103}$, R$_{104}$, R$_{105}$, R$_{106}$, R$_{107}$ and R$_{108}$ are independently selected from hydrogen, halogen, —OH, —O(R$_{113}$), —SO$_3$Na, —SO$_3$H, —N(R$_{114}$) (R$_{115}$), and —NO$_2$, R$_{113}$ is selected from hydrogen, sodium and a monovalent saturated or unsaturated, substituted or unsubstituted hydrocarbyl moiety having from 1 to 10 carbon atoms which may or may not be interrupted with a heteroatom, and R$_{114}$ and R$_{115}$ are independently selected from hydrogen and a saturated or unsaturated, substituted or unsubstituted hydrocarbyl moiety having from 1 to 10 carbon atoms which may or may not be interrupted with a heteroatom, and the first active ingredient is effective in inhibiting the production of TSST-1 from Gram positive bacteria; and wherein the first active ingredient is present in an amount of from about 0.0001 micromoles/gram of absorbent article to about 0.08 micromoles/gram of absorbent article.

8. The absorbent article as set forth in claim 7 wherein the first active ingredient has the structure of formula (I).

9. The absorbent article as set forth in claim 7 wherein the first active ingredient is selected from the group consisting of hexachlorophene, benzylparaben, benzyl salicylate, benzophenone-6, benzophenone-7, benzophenone-8, benzophenone-9, benzophenone-10, benzophenone-12, benzophenone-1, benzophenone-2, benzophenone-3, chlorophene, 2,4-diaminodiphenylamine, dichlorophene, HC Green No. 1, HC Orange No. 1, HC Red No. 1, triclosan, isopropylbenzylsalicylate, and phenyl salicylate.

10. The absorbent article as set forth in claim 7 wherein the active ingredient is selected from the group consisting of triclosan and hexachlorophene.

11. The absorbent article as set forth in claim 10 wherein the first active ingredient is hexachlorophene and the hexachlorophene is present in an amount of from 0.00024 micromoles/gram of absorbent article to about 0.08 micromoles/gram of absorbent article.

12. The absorbent article as set forth in claim 10 wherein the first active ingredient is triclosan and the triclosan is present in an amount of from about 0.0005 micromoles/gram of absorbent article to about 0.03 micromoles/gram of absorbent article.

13. The absorbent article as set forth in claim 7 wherein the first active ingredient is effective in substantially inhibiting the production of TSST-1 from *Staphylococcus aureus* bacteria.

14. The absorbent article as set forth in claim 7 wherein the first active ingredient reduces the formation of TSST-1 when the absorbent article is exposed to *S. aureus* by at least about 60%.

15. The absorbent article as set forth in claim 7 wherein the absorbent article is selected from the group consisting of a catamenial tampon, a sanitary napkin, a panty liner, an incontinent undergarment, a diaper, a wound dressing, a dental tampon, a medical tampon, a surgical tampon and a nasal tampon.

16. The absorbent article as set forth in claim 7 further comprising a pharmaceutically active material selected from the group consisting of antimicrobials, antioxidants, antiparasitic agents, antipruritics, astringents, local anaesthetics and anti-inflammatory agents.

17. The absorbent article as set forth in claim 7 further comprising an effective amount of a second active ingredient selected from the group consisting of glycerol monolaurate and myreth-3-myristate wherein said active ingredient is effective in substantially inhibiting the production of TSST-1 from Gram positive bacteria.

18. A menstrual tampon comprising an absorbent tampon material and an effective amount of a first active ingredient that is effective in inhibiting the production of TSST-1 from Gram positive bacteria, wherein the first active ingredient is selected from the group consisting of hexachlorophene, benzylparaben, benzyl salicylate, benzophenone-6, benzophenone-7, benzophenone-8, benzophenone-9, benzophenone-10, benzophenone-12, benzophenone-1, benzophenone-2, benzophenone-3, chlorophene, 2,4-diaminodiphenylamine, dichlorophene, HC Green No. 1, HC Orange No. 1, HC Red No. 1, isopropylbenzylsalicylate, and phenyl salicylate.

19. An absorbent article comprising an absorbent material and an effective amount of a first active ingredient that is effective in inhibiting the production of TSST-1 from Grain positive bacteria, wherein the first active ingredient is selected from the group consisting of hexachlorophene, benzylparaben, benzyl salicylate, benzophenone-6, benzophenone-7, benzophenone-8, benzophenone-9, benzophenone -10, benzophenone-12, benzophenone-1, benzophenone-2, benzophenone-3, chlorophene, 2,4-diaminodiphenylamine, dichlorophene, HC Green No. 1, HC Orange No. 1, HC Red No. 1, isopropylbenzylsalicylate, and phenyl salicylate.

\* \* \* \* \*